US00PP19838P2

(12) United States Plant Patent
Noordhuis

(10) Patent No.: US PP19,838 P2
(45) Date of Patent: Mar. 24, 2009

(54) ***POTENTILLA* PLANT NAMED 'YELLOW SUNRISE'**

(50) Latin Name: *Potentilla megalantha*
Varietal Denomination: Yellow Sunrise

(75) Inventor: Bart Noordhuis, Boijl (NL)

(73) Assignee: Eternal Plant Boijl B.V., Boijl (NL)

( * ) Notice: Subject to any disclaimer, the term of this patent is extended or adjusted under 35 U.S.C. 154(b) by 75 days.

(21) Appl. No.: 11/978,493

(22) Filed: Oct. 29, 2007

(51) Int. Cl.
*A01H 5/00* (2006.01)

(52) U.S. Cl. ..... Plt./237
(58) Field of Classification Search ..... Plt./237
See application file for complete search history.

*Primary Examiner*—Kent L Bell
(74) *Attorney, Agent, or Firm*—C. A. Whealy

(57) ABSTRACT

A new and distinct cultivar of *Potentilla* plant named 'Yellow Sunrise', characterized by its upright and somewhat outwardly spreading plant habit; freely branching habit; and large bright yellow-colored flowers with orange-colored bases.

2 Drawing Sheets

Botanical designation: *Potentilla megalantha.*
Cultivar denomination: 'Yellow Sunrise'.

BACKGROUND OF THE INVENTION

The present invention relates to a new and distinct cultivar of *Potentilla,* botanically known as *Potentilla megalantha,* and hereinafter referred to by the name 'Yellow Sunrise'.

The new *Potentilla* is a naturally-occurring branch mutation of an unnamed selection of *Potentilla megalantha* not patented. The new *Potentilla* was discovered and selected by the Inventor on a single plant in a controlled environment in Boijl, The Netherlands during the spring of 2003.

Asexual reproduction of the new *Potentilla* by vegetative cuttings in a controlled environment in Boijl, The Netherlands since late summer of 2003, has shown that the unique features of this new *Potentilla* are stable and reproduced true to type in successive generations.

SUMMARY OF THE INVENTION

The cultivar Yellow Sunrise has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Yellow Sunrise'. These characteristics in combination distinguish 'Yellow Sunrise' as a new and distinct cultivar of *Potentilla:*

1. Upright and somewhat outwardly spreading plant habit.
2. Freely branching habit.
3. Large bright yellow-colored flowers with orange-colored bases.

Plants of the new *Potentilla* can be compared to plants of the parent selection. Plants of the new *Potentilla* differ primarily from plants of the female parent selection in the following characteristics:

1. Plants of the new *Potentilla* are larger and more vigorous than plants of the parent selection.

2. Plants of the new *Potentilla* are more freely branching and more freely flowering than plants of the parent selection.
3. Plants of the new *Potentilla* have larger flowers than plants of the parent selection.
4. Plants of the new *Potentilla* and the parent selection differ in flower color as plants of the parent selection have lighter yellow-colored flowers without orange-colored bases.

Plants of the new *Potentilla* can be compared to plants of an unnamed selection of *Potentilla repens,* not patented. Plants of the new *Potentilla* differ primarily from plants of the unnamed selection in plant habit as plants of the unnamed selection are more outwardly spreading. In addition, plants of the new *Potentilla* have larger leaves and flowers than plants of the unnamed selection.

BRIEF DESCRIPTION OF THE PHOTOGRAPHS

The accompanying colored photographs illustrate the overall appearance of the new *Potentilla,* showing the colors as true as it is reasonably possible to obtain in colored reproductions of this type. Colors in the photographs may differ slightly from the color values cited in the detailed botanical description which accurately describe the colors of the new *Potentilla.*

The photograph on the first sheet comprises a side perspective view of a typical flowering plant of 'Yellow Sunrise' grown in a container.

The photograph on the second sheet is a close-up view of a typical flower of 'Yellow Sunrise'.

DETAILED BOTANICAL DESCRIPTION

The aforementioned photographs and following observations, measurements and values describe plants grown in Boijl, The Netherlands in containers during the spring in an outdoor nursery and under conditions which closely approximate commercial production. During the production of the plants, day temperatures ranged from about 15° C. to about 30° C. and night temperatures ranged from about 10° C. to about 15° C. Plants were about two years old when the photographs and the description were taken. In the description, color references are made to The Royal Horticultural Society Colour Chart, 1995 Edition, except where general terms of ordinary dictionary significance are used.

Botanical classification: *Potentilla megalantha* cultivar Yellow Sunrise.

Parentage: Naturally-occurring branch mutation of an unnamed selection of *Potentilla megalantha,* not patented.

Propagation:

*Type.*—By vegetative cuttings.

*Time to initiate roots.*—About 12 days at 20° C. to 21° C.

*Time to develop roots.*—About two to three weeks at 20° C. to 21° C.

*Root description.*—Fine, fibrous; color, 161D.

*Rooting habit.*—Freely branching.

Plant description:

*Plant form and growth habit.*—Upright and somewhat outwardly spreading plant habit. Vigorous growth habit.

*Branching habit.*—Freely branching, usually about seven to nine lateral branches develop per plant.

*Plant height.*—About 25 cm.

*Plant diameter* (*area of spread*).—About 40 cm to 45 cm.

Lateral branch description:

*Length.*—About 10 cm to 15 cm.

*Diameter.*—About 3 mm to 5 mm.

*Internode length.*—About 2.5 cm to 3.5 cm.

*Strength.*—Strong.

*Texture.*—Pubescent.

*Color.*—145A.

Foliage description:

*Arrangement.*—Opposite or whorled; palmately compound with three leaflets per leaf.

*Leaf length.*—About 6 cm to 6.5 cm.

*Leaf width.*—About 7.5 cm to 8 cm.

*Leaflet shape.*—Broadly ovate.

*Leaflet apex.*—Obtuse.

*Leaflet base.*—Obtuse to cordate.

*Leaflet margin.*—Irregularly lobed.

*Leaflet texture, upper surface.*—Smooth, glabrous.

*Leaflet texture, lower surface.*—Pubescent.

*Leaflet venation pattern.*—Palmate.

*Leaflet color.*—Developing foliage, upper surface: 137A. Developing foliage, lower surface: 138B. Mature foliage, upper surface: 137C; venation, 143A. Mature foliage, lower surface: 138B; venation, 138B.

*Petiole.*—Length: About 1 cm. Diameter: About 2 mm to 3 mm. Texture, upper surface: Smooth, glabrous. Texture, lower surface: Pubescent. Color, upper and lower surfaces: 145A.

Flower description:

*Flower arrangement and shape.*—Single rotate flowers arranged on panicles; flowers face upright to outwardly. Freely flowering habit, about 10 to 15 flowers per lateral branch.

*Fragrance.*—None detected.

*Natural flowering season.*—Plants begin flowering in April and continue to flower until early June in The Netherlands.

*Flower longevity on the plant.*—About two to three weeks; flowers not persistent.

*Flower buds.*—Length: About 1.5 cm to 2 cm. Diameter: About 1 cm to 1.5 cm. Shape: Ovoid. Color: 137C.

*Inflorescence size.*—Length: About 10 cm to 15 cm. Diameter: About 10 cm to 15 cm.

*Flowers.*—Diameter: About 3 cm to 3.5 cm. Depth (height): About 2 cm to 3 cm.

*Petals.*—Arrangement: Five in a single whorl. Length: About 1.5 cm. Width: About 1.4 cm. Shape: Roughly spatulate. Apex: Obtuse. Base: Attenuate. Margin: Entire. Texture, upper and lower surfaces: Smooth, glabrous; satiny. Color: When opening and fully opened, upper surface: 9A; towards the base, 17B. When opening and fully opened, lower surface: 9B.

*Sepals.*—Arrangement: Five in a single whorl. Length: About 1 cm. Width: About 5 mm. Shape: Ovate. Apex: Acute. Base: Obtuse. Margin: Entire. Texture, upper and lower surfaces: Smooth, glabrous. Color: Immature and mature, upper surface: 137A. Immature and mature, lower surface: 137C.

*Peduncles.*—Strength: Strong. Length: About 7 cm to 10 cm. Diameter: About 3 mm to 5 mm. Aspect: About 10° to about 30° from vertical. Texture: Smooth, glabrous. Color: 145A.

*Pedicels.*—Strength: Strong. Length: About 2.5 cm to 3 cm. Diameter: About 1 mm to 2 mm. Aspect: About 5° to about 10° from vertical. Texture: Smooth, glabrous. Color: 145C.

*Reproductive organs.*—Stamens: Quantity per flower: About 15 to 20. Anther shape: Oval. Anther length: About 3 mm to 5 mm. Anther diameter: About 2 mm to 4 mm. Anther color: 12A. Pollen amount: Moderate. Pollen color: 12A. Pistils: Quantity per flower: About 20. Pistil length: About 5 mm. Stigma shape: Rounded. Stigma color: 12A. Style length: About 5 mm. Style color: 12A. Ovary color: Close to 144A.

Temperature tolerance: Plants of the new *Potentilla* have been observed to tolerate temperatures from about −5° C. to about 35° C.

Pathogen/pest resistance: Plants of the new *Potentilla* have not been shown to be resistant to pathogens and pests common to *Potentilla.*

It is claimed:

1. A new and distinct *Potentilla* plant named 'Yellow Sunrise' as illustrated and described.

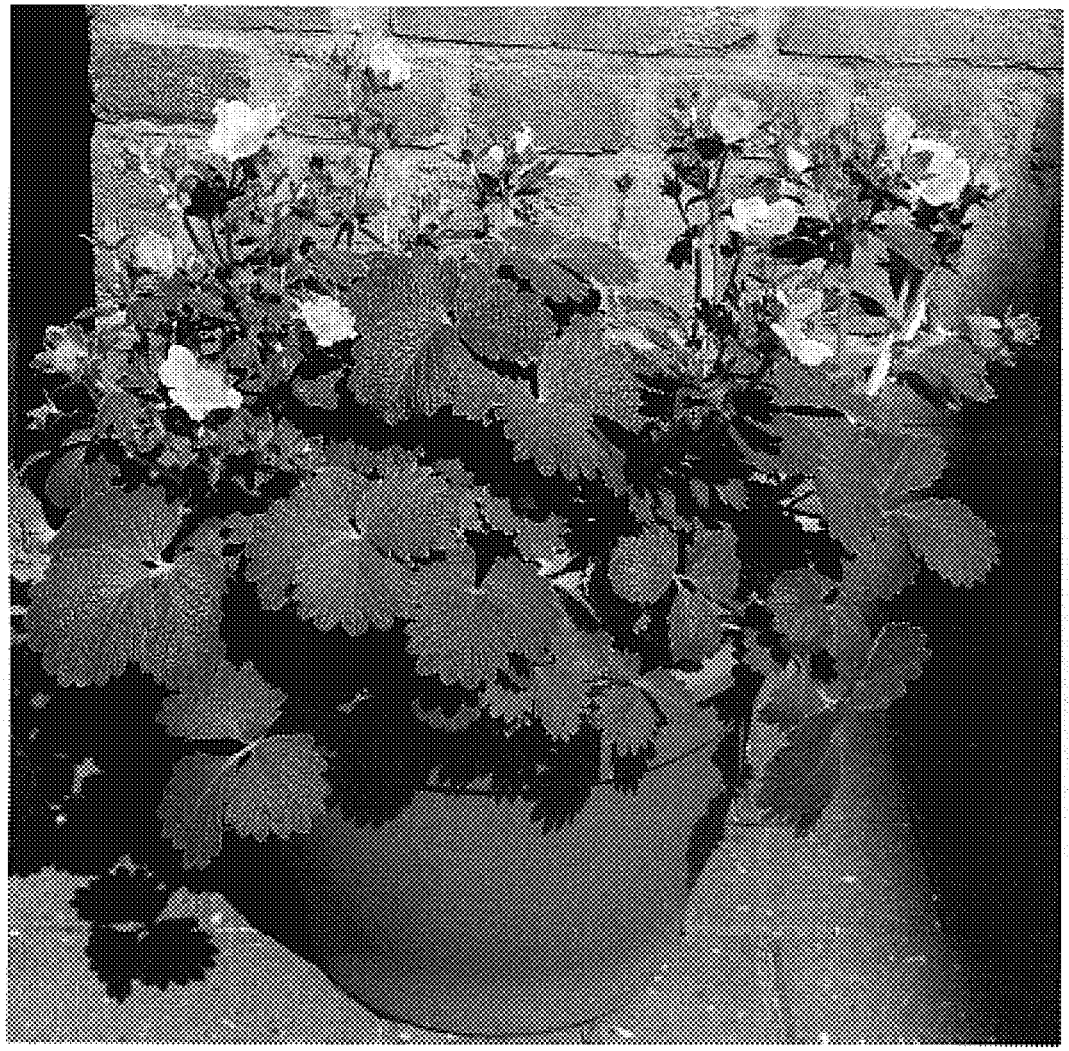

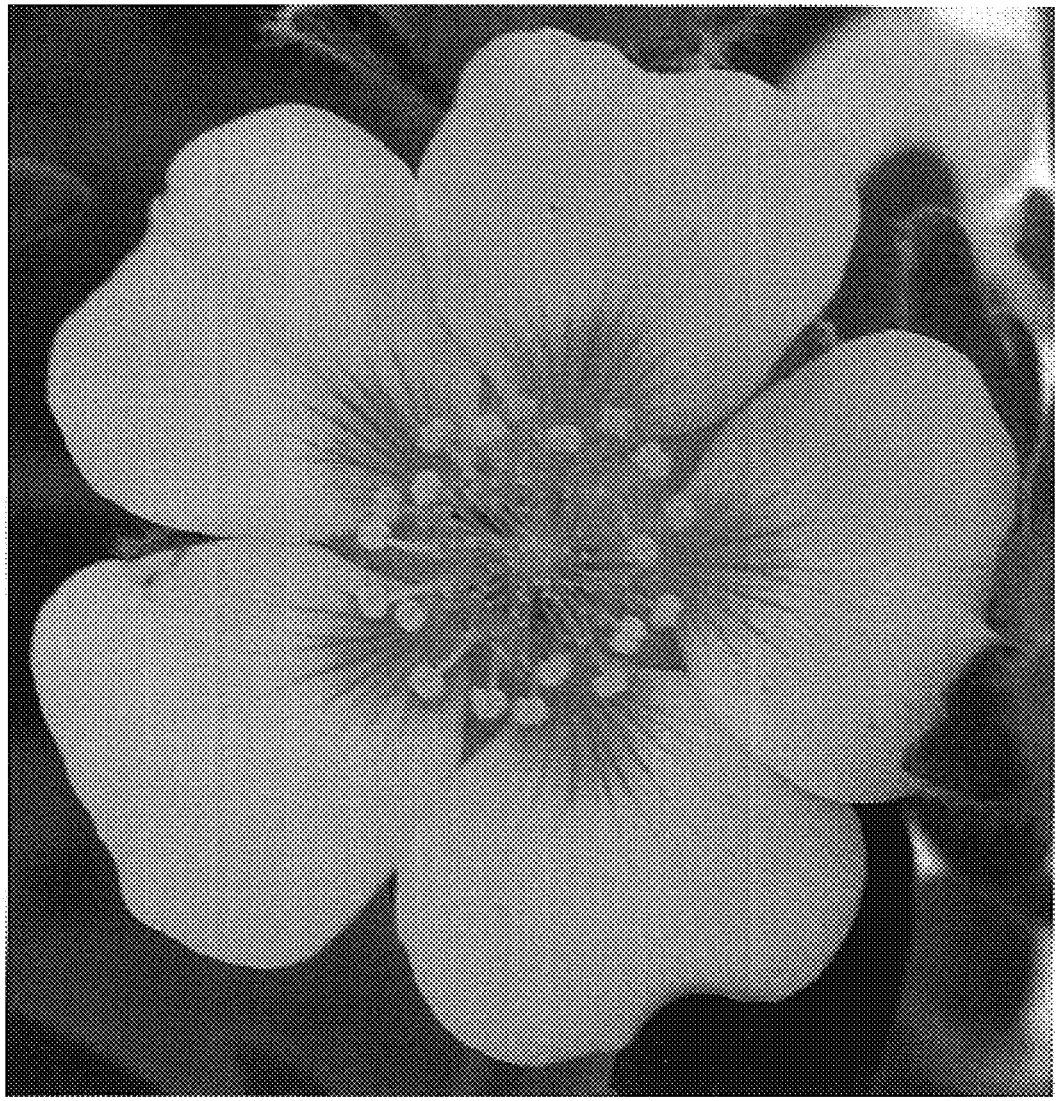

* * * * *